(12) United States Patent
Hallström et al.

(10) Patent No.: US 8,518,869 B2
(45) Date of Patent: Aug. 27, 2013

(54) PHARMACEUTICAL COMBINED PREPARATION CONTAINING A THERAPEUTIC PROTEIN

(75) Inventors: Seth Hallström, Vienna (AT); Harald Gasser, Vienna (AT)

(73) Assignee: Austria Wirtschaftsservice Gesellschaft m.b.H., Vienna (AT)

( * ) Notice: Subject to any disclaimer, the term of this patent is extended or adjusted under 35 U.S.C. 154(b) by 723 days.

(21) Appl. No.: 10/599,401

(22) PCT Filed: Mar. 24, 2005

(86) PCT No.: PCT/AT2005/000107
§ 371 (c)(1),
(2), (4) Date: Feb. 27, 2007

(87) PCT Pub. No.: WO2005/092362
PCT Pub. Date: Oct. 6, 2005

(65) Prior Publication Data
US 2007/0238641 A1    Oct. 11, 2007

(30) Foreign Application Priority Data
Mar. 29, 2004    (AT) .................................. A 556/2004

(51) Int. Cl.
*A61K 38/38*    (2006.01)
*A61K 38/00*    (2006.01)

(52) U.S. Cl.
USPC ............ 514/1.1; 514/114; 514/310; 530/362; 530/350

(58) Field of Classification Search
None
See application file for complete search history.

(56) References Cited

U.S. PATENT DOCUMENTS 6,358,918 B1 * 3/2002 Schlag et al. ..................... 514/2
6,525,017 B1 * 2/2003 Lipton .......................... 514/15.1
2002/0136763 A1 * 9/2002 Demopoulos et al. ......... 424/451

FOREIGN PATENT DOCUMENTS

EP        0 853 944 A     7/1998
WO    WO 01/65935 A       9/2001

OTHER PUBLICATIONS

Boston Medical Group (2009, updated) What is Erectile Dysfunction?, www.bostonmedicalgroup.com/erectile-dysfunction?kmas=1&kmca=bmg_erectiledysfunction&kmag=condition&kmkw=erectile+dysfunction&utm_source=google&utm_medium=ppc&utm_term=erectile_dysfunction&utm_campaign=BMG_Erectile%20Dysfunction&gclid=CJG6sJixhZsCFZpM5QodM0k8oQ, pp. 1-3.*
Tsikas et al. (2001) S-Transnitrosylation of albumin in human plasma and blood in vitro and in vivo in the rat, Biochim. Biophys. Acta., vol. 1546, No. 2, pp. 422-434.*
Hallstrom et al. (2002) S-nitroso human serum albumin treatment reduces ischemia/reperfusion injury in skeletal muscle via nitric oxide release, Circulation, vol. 105, No. 25, pp. 3032-3028.*
The Mole & Molar Mass (2010, updated) www.chemteam.info/Mole/MolarMass.html, pp. 1-2.*
Richardson G et al., "Potential therapeutic uses for S-nitrosothiols." Clinical Science (London, England : 1979), Jan. 2002, vol. 102, No. 1, pp. 99-105, XP002338091.
Crane Michael S et al: "Novel role for low molecular weight plasma thiols in nitric oxide-mediated control of platelet function." The Journal of Biological Chemistry, Dec. 6, 2002, vol. 277, No. 49, pp. 46858-46863, XP002338092.
Meyer D J et al: "Kinetics and equilibria of S-nitrosothiol-thiol exchange between glutathione, cysteine, penicillamines and serum albumin." FEBS Letters 1994 Netherlands, vol. 345, No. 2-3, 1994, pp. 177-180, XP002338093.

* cited by examiner

*Primary Examiner* — Manjunath Rao
*Assistant Examiner* — Samuel Liu
(74) *Attorney, Agent, or Firm* — Workman Nydegger

(57) ABSTRACT

A pharmaceutically combined preparation can contain a therapeutic protein having SH-groups which are nitrosated and a compound containing thiol groups and having an average molecular weight of at most 10,000.

13 Claims, 8 Drawing Sheets

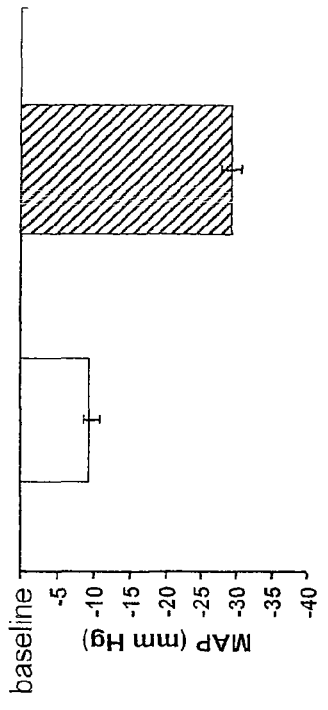
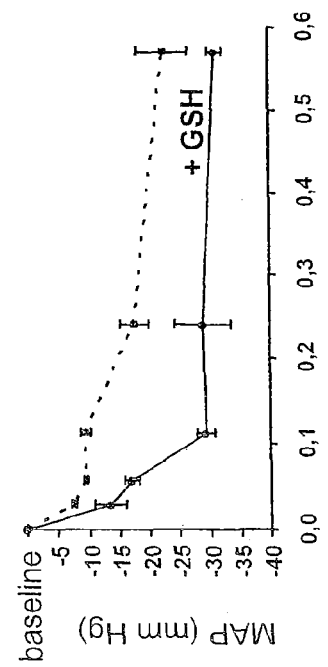
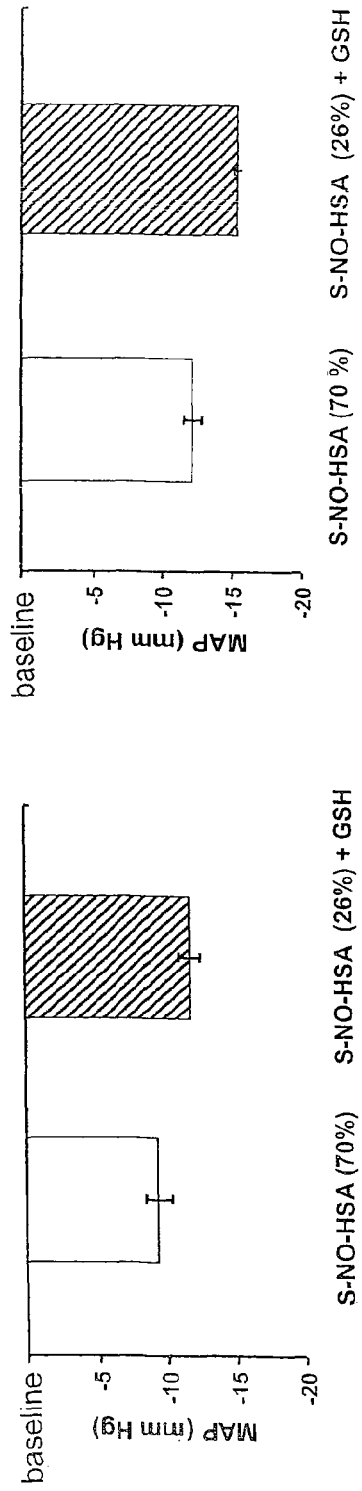

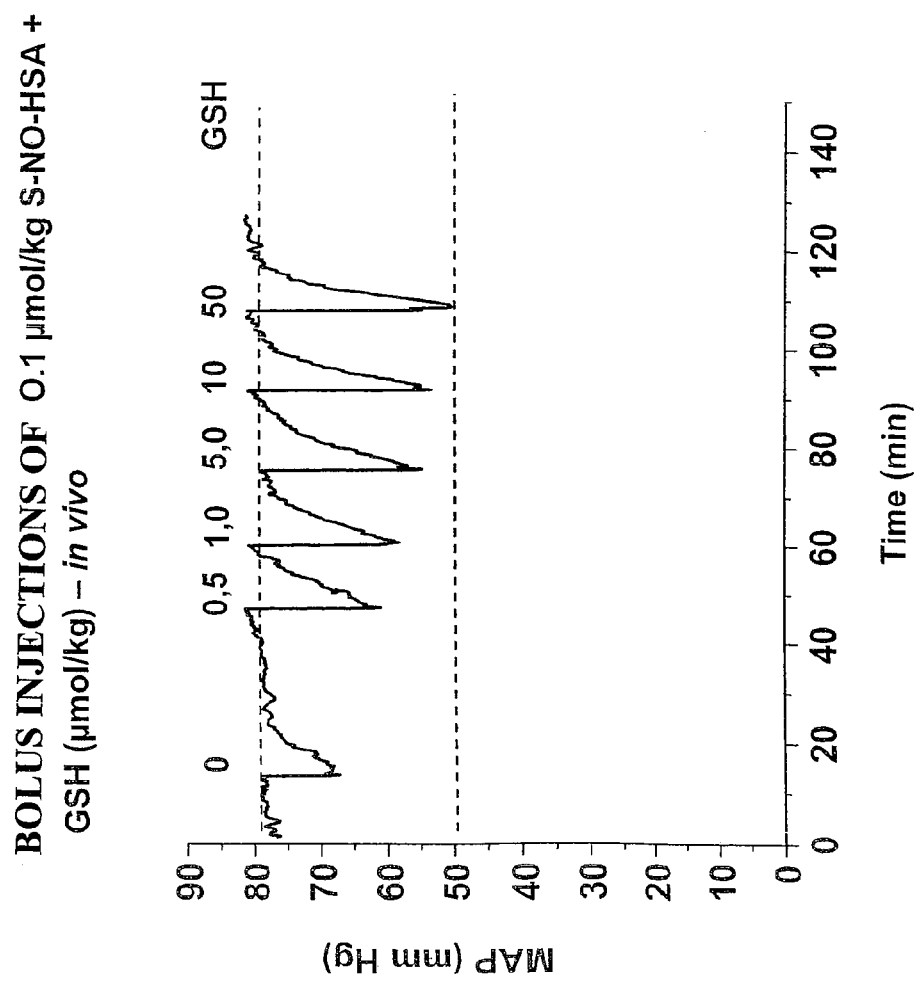

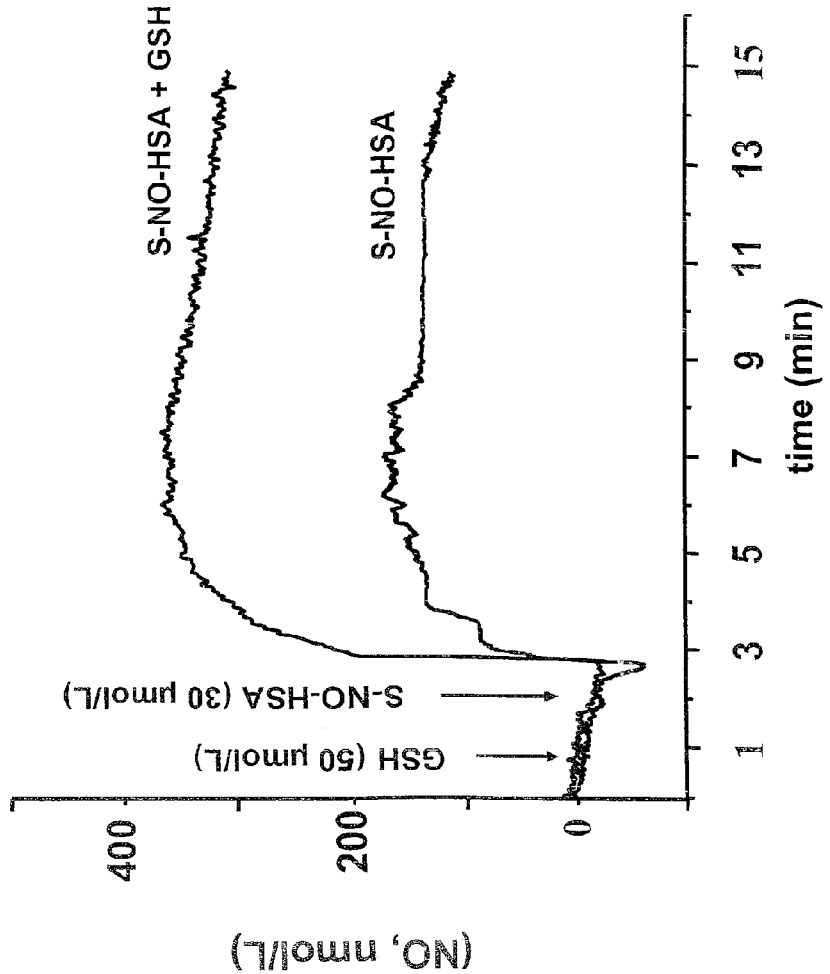

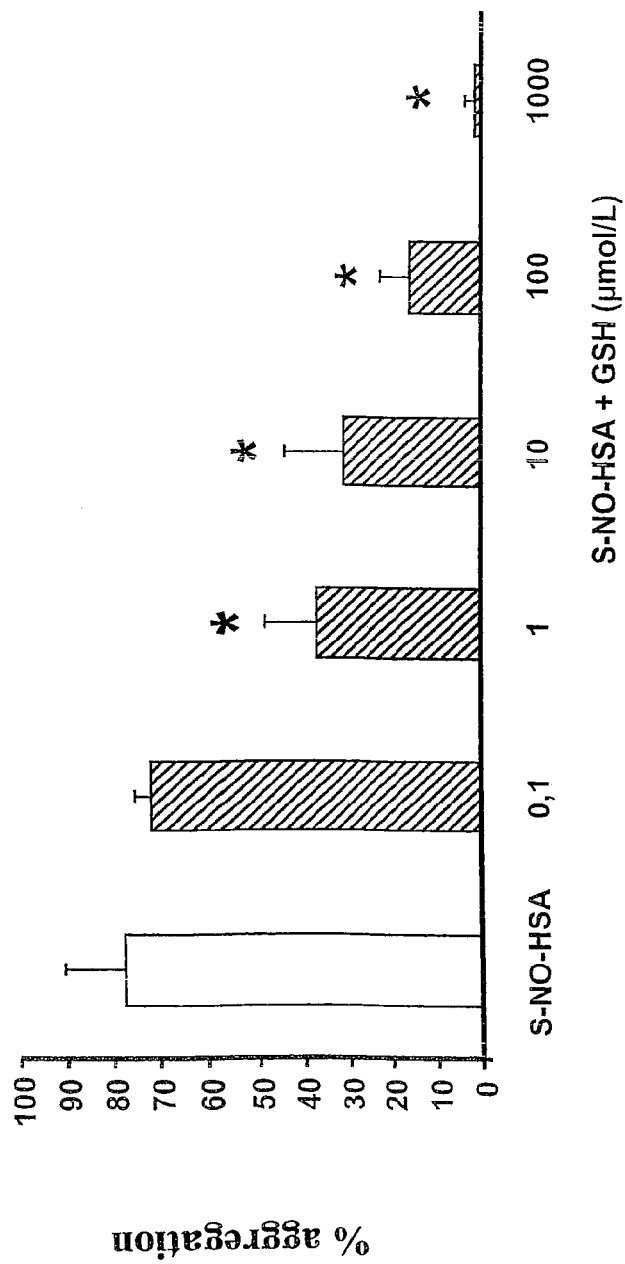

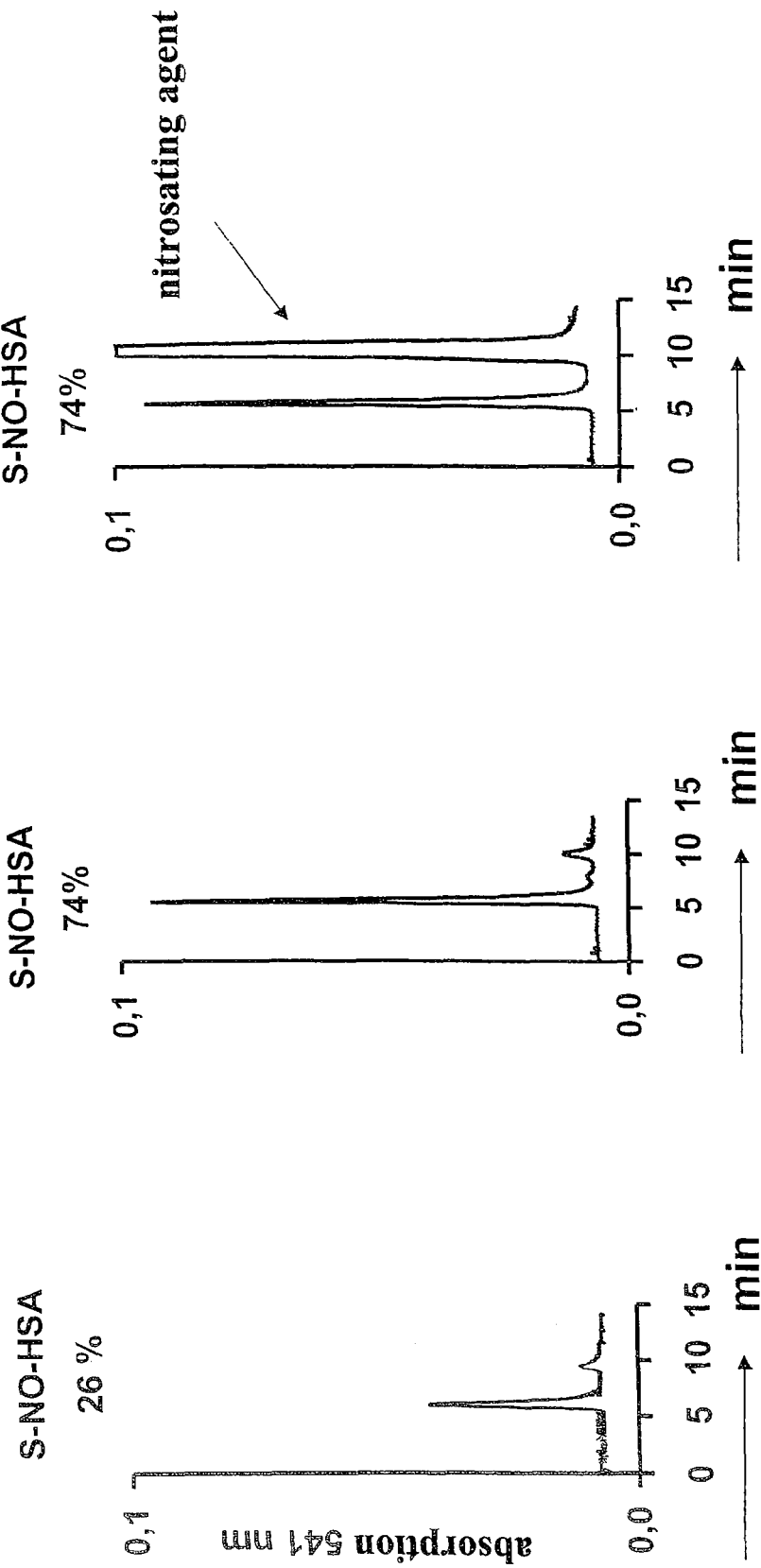

PHARMACEUTICAL COMBINED PREPARATION CONTAINING A THERAPEUTIC PROTEIN

The present invention relates to a pharmaceutically combined preparation containing a therapeutic protein having SH-groups which are nitrosated.

Nitric oxide (NO) is a gaseous molecule which is produced, among other things, in endothelial cells under normal physiological conditions. The relaxation of vascular smooth muscles, which depends on the endothelium, can primarily be traced back to NO. Thus, NO is essential for the regulation of the vasotonia. NO is furthermore involved in a number of physiological and pathophysiological processes. Deficiency in NO will thus lead, for example, to vasoconstriction and formation of oedemas in the ischaemia/reperfusion process (Huk et al., Circulation 96 (1997), 667-675; Hallström et al., Circulation 105 (2002), 3032-3038).

In preparations of proteins comprising potentially free thiol groups, only 20-35% are actually provided in the free, reduced SH form. The remaining 65 to 80% are—in particular with protein preparations which are derived from blood, or which are contacted with plasma or plasma derivatives in the course of their manufacturing process—blocked, usually by mixed S—S bonds with small compounds carrying thiol groups, for example, with free L-cysteine or glutathione, respectively (Katachalski et al., J. Am. Chem. Soc. 79 (1957), 4096-4099; DeMaster et al., Biochemistry 34 (1995), 11494-11499).

In general, with sulfur-containing groupings in proteins, one can basically distinguish between groupings which are present in a firmly bound and associated form, respectively, e.g., as intramolecular saturated disulfide bridges, and are crucial for the conformation of the proteins, and groupings which represent the potentially free thiol group(s). The latter constitute a known quantity for the respective protein. Human serum albumin (HSA), for instance, has a single potentially free thiol group per molecule in the native state, namely the cysteine in position 34. However, those potentially free thiol groups tend toward the formation of intermolecular disulfides, which is why they are also referred to as mixed disulfides. In the plasma, up to 80% of those thiol groups are provided as mixed disulfides and are thus not directly available as free thiol groups.

Reactions of the sulfhydryl group of low-molecular as well as high-molecular thiol compounds with NO, $NO_2$, $NO^+$ or $NO^-$ in the presence of oxygen result in the formation of S-nitroso compounds, so-called S-nitroso thiols. S-nitroso thiols form a group of potent bioactive compounds which stabilize physiologically formed NO and multiply the biological effects thereof. Thus, NO does not only act per se in biological systems but also via biologically active redox adducts of NO such as S-nitroso proteins, S-nitroso amino acids or other S-nitroso thiol compounds.

Experts assume that the in vivo synthesis of S-nitroso thiol compounds is effected by nitrosation of endogenous thiol-containing molecules, such as, for example, reduced glutathione, L-cysteine and serum albumin (Stamler et al., PNAS 89 (1992a), 7674-7677; Stamler et al., PNAS 89 (1992b), 444-448). The reversible S-nitrosation of those molecules might be an important cellular regulatory mechanism. Significant effects on biological functions for some thiol-containing molecules have actually been traced back to S-nitrosations. Among other things, for example, the protective blocking of the N-methyl-D-aspartate receptor in excitatory neurons (Lei et al., Neuron 8 (1992), 1087-1099; Lipton et al., Nature 364 (1993), 626-632), the inactivation of protein kinase C (Gopalakrishna et al., J. Biol. Chem. 268 (1993), 27180-27185) and certain properties of haemoglobin have been traced back to S-nitrosations (Stamler et al., Science 276 (1997), 2034-2037; Gow and Stamler, Nature 391 (1998), 169-173). The molecular mechanism for the in vivo S-nitrosation is, however, largely unknown.

Presently, at least four possible mechanisms for the S-nitrosation of compounds containing free thiol groups by NO are discussed in the literature. The first mechanism is an electrophilic attack by a reactive NO species, the nitrosonium cation ($NO^+$), on the nucleophilic sulfur atom (Stamler et al., Science 258 (1992d), 1898-1902). A second and indeed controversially discussed mechanism consists in that the S-nitrosation by NO occurs via peroxy nitrite ($ONOO^-$) or $NO_2$ (Pryor et al., J. Org. Chem. 47 (1982), 156-159; Mohr et al., FEBS Lett. 348 (1994), 223-227; Wu et al., Am. J. Physiol. 266 (1994), H2108-2113). The third, relatively new mechanism describes that S-nitrosations of thiol compounds (albumin, reduced glutathione) are caused by dinitrosyl-iron complexes (Boese et al., J. Biol. Chem. 270 (1995), 29244-29249). The fourth mechanism is an S-transnitrosation reaction or S-nitroso exchange reaction wherein an NO-group is transferred from an S-nitroso compound to a second thiol compound in exchange for an H-group (Feelisch et al., J. Cardiovasc. Pharmacol. 17 (1991), Suppl. 3, p. 25-p. 33; Field et al., JCS Chem. Commun. 6 (1978), 249-250). This reaction proceeds quickly in vitro, and the formation of S-nitroso glutathione is kinetically preferred to a substantial degree under physiological conditions. (Feelisch et al., (1991); Meyer et al., FEBS Lett. 345 (1994), 177-180; Singh et al., J. Biol. Chem. 271 (1996), 18596-18603; Tsikas et al., Anal. Biochem. 270 (1999), 231-241).

It is believed that S-transnitrosation reactions are responsible to a substantial degree for the biological effects of S-nitroso glutathione, whereby it is assumed that said process will furthermore lead to the S-nitrosation of thiol-containing proteins (Mohr et al., FEBS Lett. (1994). It has been shown that S-transnitrosation reactions between S-nitroso proteins and low-molecular thiol compounds (e.g. L-cysteine and N-acetyl-L-cysteine) occur in vivo as well (Scharfstein et al., J. Clin. Invest. 94 (1994), 1432-1439). A direct verification (in vivo) of the potentiation of the effect, such as, e.g., on the decrease in blood pressure, has, however, not been described.

BRIEF DESCRIPTION OF THE FIGURES

FIG. 1A shows the dose-dependent comparison of the decrease in mean arterial pressure (MAP) in the rabbits after bolus administrations of nitrosated serum albumin with and without a simultaneous continuous infusion of reduced glutathione (2.2 μmol/kg/min).

FIG. 1B is a representative example of the decrease in mean arterial pressure with a bolus infusion of 0.1 μmol/kg of S—NO—HSA with and without a continuous infusion of reduced glutathione (2.2 μmol/kg/min).

FIGS. 1C-1D show the decrease in mean arterial pressure with two different dosages of a nitrosated serum albumin preparation having a high degree of nitrosation (70%) and a native serum albumin nitrosated equimolarly to the freely available thiol group and having a low degree of nitrosation (26%), with a simultaneous infusion of reduced glutathione.

FIG. 1E is a representative example of the decrease in mean arterial pressure by in vivo bolus injections of 0.1 μmol/kg of S—NO—HSA with variable concentrations of glutathione (GSH).

FIG. 2B shows a representative example of the in vitro measurement of the potentiation of the NO-release of a nitrosated serum albumin preparation by reduced glutathione.

FIG. 3A shows the dose-dependent potentiation of the inhibition of the collagen-induced platelet aggregation by S—NO—HSA (2-4 μmol/L) with reduced glutathione.

FIGS. 4A-4B show absorption at 541 nm verses time for 26% S-NO-HSA (FIG. 4A), 74% S-NO-HSA (FIG. 4B), and 74% S-NO-HSA with nitrosating agent.

Figure 1F:
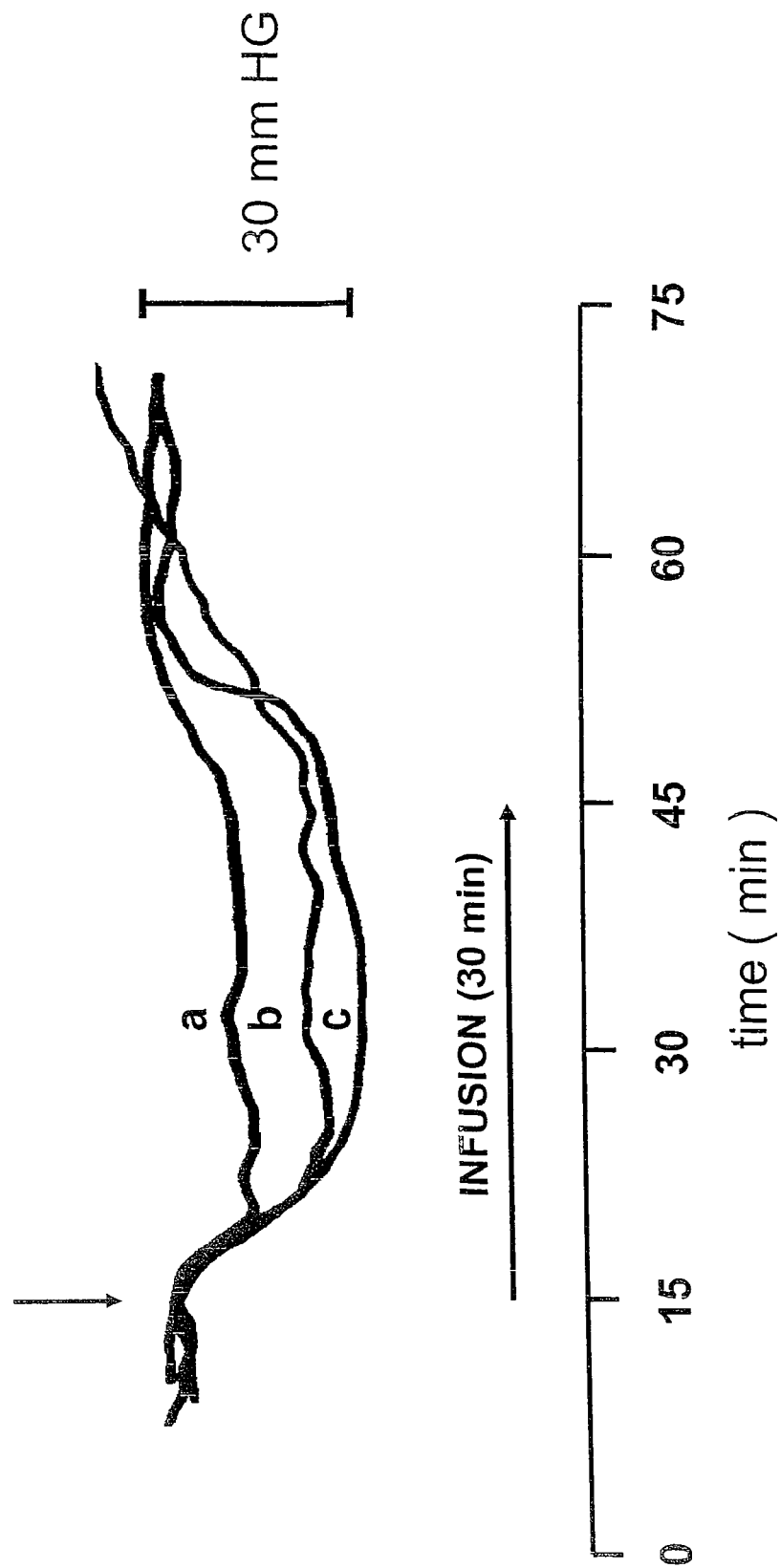
FIG. 1F is a representative example of the decrease in mean arterial pressure by a simultaneous, continuous infusion of 0.05 μmol/kg/min of S—NO—HSA, with an increasing concentration of reduced glutathione (a: 0.0 μmol GSH/kg/min, b: 0.1 μmol GSH/kg/min, c: 0.3 μmol GSH/kg/min).

It is the object of the present invention to increase the physiological effect of proteins containing nitrosated sulfhydryl groups (SH-groups).

According to the invention, said object is achieved by a pharmaceutically combined preparation which contains a therapeutic protein having SH-groups which are nitrosated and a compound containing thiol groups and having an average molecular weight of at most 10,000. By the term "thiol groups", sulfhydryl groups (—SH) and disulfide groups (—S—S—) are understood.

A preferred embodiment of the combined preparation according to the invention consists in that at least 90% of the present SH-groups are nitrosated.

As the therapeutic protein having nitrosated SH-groups that is contained in the pharmaceutically combined preparation according to the invention, S-nitroso albumin, S-nitroso orosomucoid, S-nitroso plasminogen activator, S-nitroso fibrinogen, S-nitroso Lys-plasminogen or S-nitroso haemoglobin is particularly preferred.

As the compound containing thiol groups that is contained in the preparation, reduced glutathione (GSH), L-cysteine, N-acetyl cysteine, L-cysteinyl glycine, γ-glutamyl cysteine, penicillamine, penicillamide, N-acetyl penicillamine, N-acetyl penicillamide, homocysteine, captopril, dihydrolipoic acid and/or the oxidized form thereof, which, after administration, is reduced in vivo, is/are particularly preferred.

It has been shown that a further preferred embodiment of the pharmaceutically combined preparation according to the invention contains S-nitroso albumin as the therapeutic protein having nitrosated SH-groups and reduced glutathione as the compound containing thiol groups.

Furthermore, a compound occurring in human blood and tissue, in particular reduced glutathione, L-cysteine, L-cysteinyl glycine, γ-glutamyl cysteine or dihydrolipoic acid, is particularly preferred as the compound containing thiol groups.

A further embodiment of the pharmaceutically combined preparation according to the invention consists in that a therapeutic protein obtained by nitrosation is contained in which the degree of nitrosation is made up of S-nitrosation by at least 90% and of N,O,C-nitrosation by at most 10%.

In principle, the pharmaceutical preparation according to the invention can contain, for the protein component, any proteins having a "free" thiol group, however, therapeutically applicable proteins are preferred for the purposes of the present invention, wherein physiological proteins and human proteins derived from blood, respectively, such as albumin, orosomucoid, plasminogen activator (e.g. t-PA), fibrinogen, Lys-plasminogen or haemoglobin or also mixtures of such proteins which are nitrosatable or have been nitrosated according to the invention, respectively, have to be regarded as particularly preferred.

Accordingly, the pharmaceutical preparation according to the invention can contain, for the low-molecular thiol component, any low-molecular thiol compound, such as reduced glutathione, L-cysteine, N-acetyl-L-cysteine, L-cysteinyl glycine, γ-glutarnyl cysteine, penicillamine or amides, respectively, N-acetyl penicillamine or amides, respectively, homocysteine, captopril (D-2-methyl-3-mercaptopropanoyl-L-proline) and reduced thioctic acid (dihydrolipoic acid), however, low-molecular thiol compounds occurring in blood (plasma), such as, e.g., reduced glutathione, L-cysteine, L-cysteinyl glycine, γ-glutamyl cysteine and dihydrolipoic acid, are preferred.

The production of proteins containing nitrosated thiol groups is described, for instance, in EP-A 0 853 944.

Nitrosation is preferably performed such that only the freely available thiol groups are nitrosated and foreign nitrosations are avoided (equimolar nitrosation). This can be done successfully since primarily free SH-groups are preferably nitrosated and foreign nitrosations occur in N,O,C-atoms of the proteins only if an excess of nitrosating agent is present. For example, N- and C-nitroso compounds are suspected to be carcinogenic and also have a release kinetics of the NO-group which is different from that of S-nitroso compounds (see Zhang et al., J. Biol. Chem. 271 (24) (1996), 14271-14279), which is why, in a preferred embodiment of the preparation according to the invention, an N,O,C-nitrosation degree of the proteins in the preparation of at most 10% is provided.

Although it is possible for the protein component to subject also crude fractions such as plasma or early plasma fractions and broth cultures, respectively, to equimolar nitrosation, the proteins are preferably made available in a purified form. The degree of purity should preferably be appropriate so that the proteins can be administered pharmaceutically. Therefore, a protein for nitrosation having a degree of purity of at least 80%, in particular of at least 90% (% by weight), based on the protein, is provided for the protein component of the preparation according to the invention. Higher values are of course also preferred. This purified protein can of course be formulated into a pharmaceutical preparation with further proteins.

The protein component in the preparation according to the invention can thus constitute a mixture of various equimolarly nitrosated proteins but can also constitute a mixture of a non-nitrosated protein and an equimolarly nitrosated protein. Preferably, the pharmaceutical preparation contains S-nitroso human serum albumin as a protein component and reduced glutathione. For a protein component hybrid, the pharmaceutical preparation preferably contains S-nitroso human serum albumin and haemoglobin. For the preparation according to the invention, the protein component is preferably made available in a higher purity than the non-nitrosated protein component. Thus, human serum albumin is, for example, often administered as a pharmaceutical preparation in a purity of at least 80% of the total protein. An analogous or higher degree of purity is preferred also for the S-nitrosated protein in the preparation. For the nitrosated protein, an additional purification step is therefore provided after the nitrosation of the protein component.

In the combined preparation according to the invention, the low-molecular thiol compounds are preferably provided in a purified form. The degree of purity should preferably be appropriate so that the low-molecular thiol compound in the preparation can be administered pharmaceutically. For the low-molecular thiol compound of the preparation according to the invention, a degree of purity of at least 90%, in particular of at least 95% by weight, based on the low-molecular thiol compound, is thus provided. Higher values are of course also preferred.

The pharmaceutical preparation according to the invention is formulated preferably in a pharmaceutically acceptable buffer solution, optionally comprising pharmaceutically acceptable stabilizers. For example, sodium caprylate and/or sodium acetyl tryptophanate is/are used as a stabilizer. Thereby, it is normally possible to resort to formulations as used for the application of the protein component as a non-nitrosated product. The preparations can also be made available as a spray or in a form suitable for topical application. In particular, the preparation is made available in a form suitable for intravenous administration. Regarding the protein component, an IV-compatible preparation is characterized especially by a low content of aggregates or is free from aggregates, respectively.

It is understood that often arrangements must be made also for the storage of the preparation according to the invention so that said preparation will remain stable over an extended period of time. Thus, for storage purposes, the preparation according to the invention is preferably provided in frozen or lyophilized form in which it has a sufficiently long storage stability. Hereby, it is possible to store the low-molecular thiol compound and the nitrosated protein of the preparation according to the invention both in combined and in separate form.

It has been shown that, e.g. for proteins derived from plasma or blood, in particular for albumin or haemoglobin, stability is greatest in a solution at a pH-value of roughly between 6 and 7 in a suitable buffer system (e.g. Ringer's solution). Regarding low-molecular thiol compounds, in particular reduced glutathione and L-cysteine, it has been shown, on the other hand, that stability is greatest in a solution below a pH-value of 7.

The pharmaceutical preparation based on a protein comprising nitrosated thiol groups and a low-molecular thiol compound is stable if stored separately in the lyophilized state.

In contrast to the known method (e.g.: Stamler et al., (1992a), nitrosation can preferably be performed such that, exclusively after determining the "free" thiol content of the proteins, nitrosation is performed equimolarly to this amount of "free" thiol groups and, at the same time, a low-molecular thiol compound is provided. In doing so, both native thiol-containing proteins and thiol-containing proteins in which the "free" thiol groups are deblocked by a specific process come into consideration as a protein component.

The separation of reactants and reaction products, respectively, occurs after the nitrosation reaction and preferably to a quantitative extent or up to a value below the detection limit, respectively.

In a further preferred embodiment, the preparation according to the invention is also characterized by a low content of aggregates in the protein component. In particular, the amount of aggregates in the pharmaceutical preparation is below 20%, preferably below 10%, most preferably below 5%.

The nitrosation of the thiol-containing proteins is performed under aerobic conditions, in particular if acidic sodium nitrite is used for the operation.

The nitrosation is preferably carried out with an agent selected from $HNO_2$, HNO, NOCl, $NO^+$, $RNO_2$, $N_2O_3$, $N_2O_4$, $NO_2^-$— and NO-radical and in an acid medium. Organic NO-donors can also be used.

In order to keep the degree of N- and C-nitrosation as low as possible, nitrosation with an agent should be carried out equimolarly to the content of "free" thiol groups in the protein, based on the release of NO. Of course, a smaller ratio of agent can also be added for the nitrosation, based on the content of thiol groups in the protein, a ratio of 1:1 is preferred, however. Since the S-nitrosation proceeds preferentially and much faster than N- and C-nitrosations, with an equimolar nitrosation, a minimum N- and C-nitrosation degree of the protein is ensured. Furthermore, the duration of nitrosation should be as short as possible. Thus, nitrosation is preferably carried out within a period of 2 minutes up to several hours, preferably 30 minutes, at a temperature of between 15-30° C., preferably at room temperature, in an aqueous solution at a pH of 0.3 to 3.5, most preferably at a pH of 1.0 to 3.0, preferably in the acid range up to a pH of 1.5.

All kinds of protein fractions can be used as a starting material for the protein component, hence in particular also blood, plasma, serum, a plasma fraction or a purified protein fraction, but also culture supernatants or respective extracts. If, however, substances are contained in the starting material which might have a negative impact on the nitrosation step, such as, for example, low-molecular proteins containing thiol groups or compounds containing thiol groups, those substances should preferably be separated. Preferred plasma fractions are those according to the Cohn fractionation and in particular the Cohn II- and III-fractions or the Cohn IV-fraction.

Within the scope of the process according to the invention, quite a number of further purification steps can also be provided for the protein component at arbitrary points in the process.

A further purification step selected from precipitation, gel filtration, diafiltration, ultrafiltration and chromatographic purification can be provided. For example, albumin is purified by means of ion exchange chromatography.

In particular, it may be provided that a purification step is performed after the nitrosation of the protein so that the substances used therein neither influence each other nor are present in the completely nitrosated protein component.

Preferably, said purification step is carried out in the form of a chromatographic purification, especially by means of gel permeation chromatography.

A treatment for the inactivation of viruses is preferably carried out already prior to nitrosation, but may also be performed terminally, i.e., following nitrosation.

After nitrosation, the protein component of the combined preparation according to the invention can be processed into a pharmaceutical preparation in a manner known per se. Regarding the protein component, the formulation guidelines (see pharmacopoeia) for the non-nitrosated protein preparation are normally observed.

The low-molecular thiol compound, preferably reduced glutathione or L-cysteine, is provided as a highly purified substance in a form which can be administered pharmaceutically and is applied IV simultaneously with the purified, nitrosated protein component.

Preferred medical applications of said combined preparation according to the invention comprise the manufacture of a combined preparation for improving the perfusion and microcirculation, respectively, preferably in vital organs such as, for example, in the brain (cerebral ischaemia, ischaemic insult), in the heart (myocardial infarction), in the kidney or in the extremities or in the entire organism, respectively. Thus, the combined preparation according to the invention can generally be used for preventing and treating, respectively, ischaemia and reperfusion injury. The combined preparation according to the invention is also suitable for treating shock, in particular traumatic, hypovolaemic and haemorrhagic shock, respectively, or neurogenic shock.

The combined preparation according to the present invention can be used in various surgical fields, for example in transplantation surgery and in all surgical operations involving a subsequent reperfusion. It is particularly suitable for the treatment and/or prophylaxis of restenosis following angioplasty.

The combined preparation can also be used for the treatment and/or prophylaxis of thrombotic conditions, i.e., conditions associated with an adhesion/aggregation of blood platelets. In a preferred embodiment, the S—NO-tissue plasminogen activator can be used as a thrombolytic agent.

The combined preparation can furthermore be used for the relaxation of non-vascular, smooth muscles, such as, e.g., smooth muscles in the respiratory tract. Thus, the preparation can be used, according to the present invention, for the treatment and/or prophylaxis of respiratory tract diseases. It may also be useful for the diagnosis and/or treatment of erectile dysfunctions in men.

A further, substantially preferred medical use of the combined preparation according to the invention comprises the manufacture of a combined preparation for the controlled reduction of blood pressure, such as, e.g., in hypertonic crises (i.e., chronic and acute hypertension crises, respectively). Hereby, a higher dosage will normally be used than for the prevention and treatment, respectively, of ischaemia and reperfusion injury.

Regarding the protein component, the medical combined preparation is preferably provided in a dosage which, except in case of albumin, corresponds to that of non-nitrosated protein. If albumin is provided as the protein component, the dosage depends mainly on the medical indication. For the prevention and treatment, respectively, of ischaemia and reperfusion injury, a dosage of 0.035-1.0 µmol/kg/h is recommended, depending on the respective S-nitroso level of the albumin preparation. For reducing the blood pressure, higher dosages are to be applied (e.g. up to 10 µmol/kg/h of S—NO-albumin with a degree of S-nitrosation of 26%). For the low-molecular thiol compound (e.g. reduced glutathione), a dosage of 12-140 µmol/kg/h is recommended. The amount or dosage, respectively, to be administered depends on the patient's needs, e.g., on parameters such as haematocrit, oxygenation, mean arterial and venous blood pressure and pulmonary arterial pressure, respectively, and can be quite different on a case-to-case basis. For the platelet adhesion/aggregation-inhibiting effect, also substantially lower dosages can be used.

A particular advantage of the combined preparation according to the invention is that at least the same efficiency is achieved with proteins containing thiol groups as with monopreparations of proteins containing thiol groups, wherein the freely available thiol group has been raised to 90% free SH-groups per mole of protein, using a reductive pretreatment. In procedural terms, the reductive pretreatment is thereby avoided. An equimolar nitrosation to the freely available thiol group guarantees the same degree of purity of the active component of the protein preparation (N-, C-, O-nitrosation <5%). Both albumin (4-5 g/dL plasma) and reduced L-glutathione (<5 µmol/L) are naturally occurring plasma components. The physiologically occurring, reduced L-glutathione level in the plasma leads to a limitation of the naturally occurring transnitrosation reaction. By providing reduced L-glutathione, the release of the active substance NO of the S-nitrosated protein component is controllable even in a dose-dependent way by the reduced L-glutathione.

It is understood that, regarding the protein component in general, the combined preparation according to the invention can also be used for any indication of the non-nitrosated proteins, since their physiological effect is maintained despite nitrosation. In addition, however, conditions requiring the provision of an increased NO-content constitute preferred indications for the combined preparations according to the invention.

Manufacturing human serum albumin nitrosated equimolarly to the freely available thiol group and providing reduced glutathione:

a) Determining the ratio of free SH-groups per mole of protein prior to nitrosation.

The ratio of free SH-groups per mole of protein was determined by means of the Ellman reagent (Ellman G. L., Arch. Biochem. Biophys. 82 (1959), 70-77) according to Sedlak and Lindsay, Anal. Biochem. 25 (1968), 192-205.

For example, for human albumin 20% (manufacturer: Baxter), an SH-group content of 26% (mol/mol, SH-group content relative to protein) has been determined. After a reductive pretreatment of a further human albumin preparation (AT 405 135; U.S. Pat. No. 6,124,255 and U.S. Pat. No. 6,358,918), values of up to 95% are achievable and detectable.

b) Equimolar nitrosation to the free SH-group content of the respective human albumin preparation The nitrosation of the albumin preparations was performed equimolarly to the content of free SH-groups (ratio: 1:1 to a maximum of 1:1.2 molarly to the determined value) with $NaNO_2$ in 0.2 mol/L HCl at pH 1.5-2.5 for a duration of 15-30 min at room temperature. Subsequently, neutralization was effected with 1 mol/L NaOH. In order to separate undesired reactants, a preparative gel permeation chromatography was carried out using a stationary phase of beads with a heteroporous, swollen network of a Toyopearl TSK HW 40 (F) gel. Elution was effected with bidistilled water at 4° C. Subsequently, the purified fraction containing S-nitroso albumin (S-NO-albumin/albumin) was lyophilized.

Determining the S-nitroso level of the protein fraction with HPLC, using Saville and Griess reactions The analysis can be performed prior to or after the purification by means of preparative gel permeation chromatography. In this method, surplus nitrosating agent and buffer substances, if present, are separated from S—NO-albumin albuminusing a gel permeation column (Toyopearl TSK HW-40-S). Subsequently, the NO-group is cleaved selectively from an S-nitrosated compound (RS—NO; where R represents a compound having the S-nitrosated group) by $Hg^{2+}$ in a postcolumn derivatization process via the Saville reaction (Saville B., Analyst 83 (1958), 670-672). Simultaneously, the nitrite which has developed is detected photometrically at 541 nm by means of a colour reaction (Griess reaction; Griess, Ber. Dtsch. Chem. Ges. 12 (1897), 426-428). The chromatograms (FIG. 4) show equimolarly nitrosated S—NO—HSA preparations with different S-nitroso levels: a) human albumin nitrosated equimolarly to the free SH-group and having a content of free SH-groups per mole of protein of 26%; b) human albumin nitrosated equimolarly to the free SH-group, which, due to a reductive pretreatment, had a content of free SH-groups per mole of protein of 74%; c) analogous to b) except for that nitrosation did not occur in an equimolar fashion but with a 6-fold molar excess of nitrosating agent.

According to the Saville principle, the percentages indicated constitute the actual degrees of S-nitrosation on the protein. When determining the degree of S-nitrosation prior to the preparative purification, a possible second peak in the chromatogram results from the surplus nitrosating agent (chromatogram c). With albumin preparations nitrosated equimolarly to the free SH-group, nitrite is detectable only in trace amounts.

Providing reduced glutathione

Reduced glutathione produced by peptide synthesis and having a degree of purity of at least 95% was provided as the low-molecular thiol compound.

The effect of the combined preparation according to the invention is described hereinbelow by way of a preferred embodiment.

EXAMPLE 1

In Example 1, the decrease in mean arterial pressure by applying a combined preparation according to the invention consisting of a nitrosated serum albumin preparation and reduced glutathione is shown by way of a rabbit model. For the purpose of comparison, the effect of a nitrosated serum albumin preparation which was applied without reduced glutathione is shown.

The rabbit was anaesthetized, whereby the anaesthesia was initiated with ketaset (50 mg/kg; bolus) and xylasine (5 mg/kg; bolus) and was maintained with a continuous infusion of ketaset (35 mg/kg/h) and 5 mg of xylasine (5 mg/kg/h), dissolved in physiological saline (5 mL/h), via the vena auricularis. After tracheotomy and intubation, the rabbits were attached to the respirator (Ventilator Harvard Apparatus-INSPIRA ASV) (tidal volume=0.0062×body weight (kg)$^{1.01}$, respiration rate=53.5×body weight (kg)$^{0.26}$).

The mean arterial pressure (MAP) was measured in the arteria femoralis by means of a pressure transducer (amplifier unit—TAM-A and Isotec pressure transducer; Hugo Sachs Elektronik). The results are illustrated in FIGS. 1a-f.

FIG. 1a shows the dose-dependent comparison of the decrease in mean arterial pressure (MAP) in the rabbits after bolus administrations of nitrosated serum albumin with and without a simultaneous continuous infusion of reduced glutathione (2.2 µmol/kg/min). Infusion: vena femoralis (n=3 per data point; mean value±standard deviation).

FIG. 1b is a representative example of the decrease in mean arterial pressure with a bolus infusion of 0.1 µmol/kg of S—NO—HSA with and without a continuous infusion of reduced glutathione (2.2 µmol/kg/min).

FIGS. 1c and 1d show the decrease in mean arterial pressure with two different dosages of a nitrosated serum albumin preparation having a high degree of nitrosation (70%) and a native serum albumin nitrosated equimolarly to the freely available thiol group and having a low degree of nitrosation (26%), with a simultaneous infusion of reduced glutathione (n=3 per data point; mean value±standard deviation).

FIG. 1e is a representative example of the decrease in mean arterial pressure by in vivo bolus injections of 0.1 µmol/kg of S—NO—HSA with variable concentrations of GSH. Infusion: vena femoralis.

FIG. 1f is a representative example of the decrease in mean arterial pressure by a simultaneous, continuous infusion of 0.05 µmol/kg/min of S—NO—HSA, with an increasing concentration of reduced glutathione (a: 0.0 µmol GSH/kg/min, b: 0.1 µmol GSH/kg/min, c: 0.3 µmol GSH/kg/min). S—NO—HSA was infused via the venajugularis, and reduced glutathione was infused via the second vena auricularis (or vena femoralis).

EXAMPLE 2

In Example 2, the potentiation of the NO-release of a nitrosated serum albumin preparation by providing a low-molecular thiol compound is demonstrated by the example of reduced glutathione. The NO-concentration was measured in vitro.

Figure 2A:
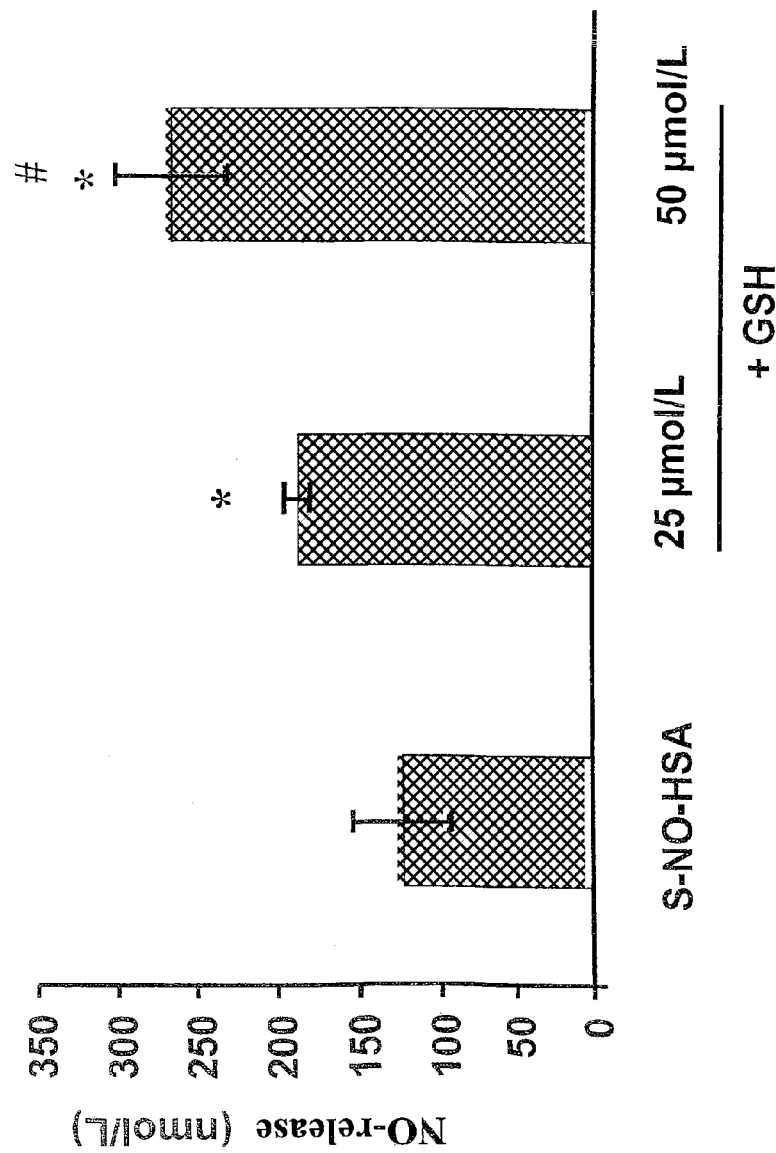
FIG. 2A shows the concentration-dependent potentiation of the NO-release of a nitrosated serum albumin preparation by reduced glutathione, measured in vitro with a porphyrinic microsensor.

FIG. 2a shows the concentration-dependent potentiation of the NO-release of a nitrosated serum albumin preparation by reduced glutathione, measured in vitro with a porphyrinic microsensor (S—NO—HSA: 30 µmol/L; n=6, mean value±standard deviation; *P<0.05 vs S—NO—HSA; #P<0.05 vs 25 µmol/L GSH).

FIG. 2b shows a representative example of the in vitro measurement of the potentiation of the NO-release of a nitrosated serum albumin preparation by reduced glutathione.

EXAMPLE 3

The effect of a preferred embodiment of the combined preparation according to the invention on the platelet aggregation is illustrated by way of Example 3.

The platelet aggregation was performed with human plasma rich in thrombocytes (TRP) in a Dual Kanal Chronolog Aggregometer basically according to the method by Born (1969). At the onset of each experiment, the exact dose of collagen was determined for the aggregation induced by collagen (~1 µg collagen/mL TRP) (95-100% inhibition of the collagen-induced aggregation by 300 µmol/L of acetylsalicylic acid). In the experiments, increasing concentrations of reduced glutathione were pre-incubated in the aggregometer for one minute primarily with TRP, and after one minute S—NO—HSA (2-4 µmol/L; concentration which causes a 20% inhibition of the collagen-induced aggregation) was added. After another minute, aggregation was induced with collagen. Control experiments with collagen alone were carried out after every second to third measurement. The results are illustrated as % aggregation relative to the aggregation induced by collagen (100%) (mean value±standard error). The final concentrations in the aggregation vessel are indicated in the images. In experiments with different thiol- and non-thiol-containing substances (N-acetyl-L-cysteine, ascorbic acid, DL-homocysteine, taurine, L-cysteine), pre-incubation was effected primarily with those substances, in analogy to the trials using reduced glutathione.

FIG. 3a shows the dose-dependent potentiation of the inhibition of the collagen-induced platelet aggregation by S—NO—HSA (2-4 µmol/L) with reduced glutathione (n=6; *P<0.05 versus S—NO—HSA).

Figure 3B:
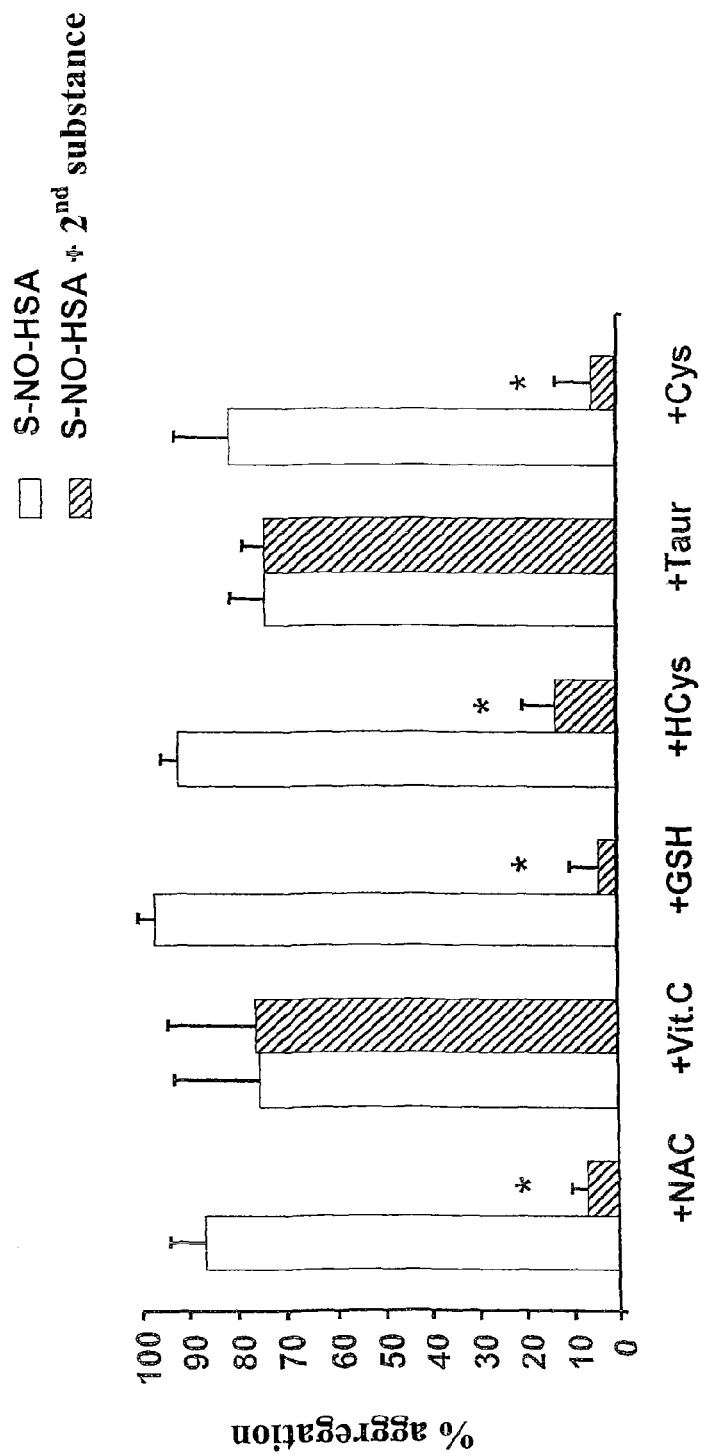
FIG. 3B the effect of N-acetyl cysteine (1 mmol/L), ascorbic acid (Vit.C; 200 μmol/L), reduced glutathione, homocysteine, taurine and cysteine (1 mmol/L in each case) on the inhibition of the collagen-induced platelet aggregation by S—NO—HSA (2-4 μmol/L).

FIG. 3b shows the effect of N-acetyl cysteine (1 mmol/L), ascorbic acid (Vit.C; 200 µmol/L), reduced glutathione, homocysteine, taurine and cysteine (1 mmol/L in each case) on the inhibition of the collagen-induced platelet aggregation by S—NO—HSA (2-4 µmol/L) n≧5 (taurine, n=3); *P<0.01 versus S—NO—HSA.

The invention claimed is:
1. A method for the treatment of ischemia comprising:
administering a pharmaceutical preparation to a subject in need thereof, the pharmaceutical preparation comprising: a therapeutic protein having nitrosated SH-groups, wherein the therapeutic protein is S-nitroso albumin in one or more dosage 0.035-1.0 µmol/kg/h; and reduced glutathione in one or more dosage of 12-140 µmol/kg/h so as to accelerate nitric oxide release by the S-nitroso albumin compared to administering S-nitroso albumin alone.

2. The method according to claim 1, wherein at least 90% of the SH-groups of the S-nitroso albumin are nitrosated.

3. The method according to claim 2, wherein in the S-nitroso albumin the degree of nitrosation is made up of S-nitrosation by at least 90% and of N-nitrosation, O-nitrosation, or C-nitrosation by 10%, or less.

4. The method according to claim 1, wherein in the S-nitroso albumin the degree of nitrosation is made up of S-nitrosation by at least 90% and of N-nitrosation, O-nitrosation, or C-nitrosation by 10%, or less.

5. The method according to claim 1, wherein administering the reduced glutathione together with the S-nitroso albumin accelerates nitric oxide release by the S-nitroso albumin of at least 50% compared to administering the S-nitroso albumin alone.

6. The method according to claim 1, wherein administering the reduced glutathione together with the S-nitroso albumin results in reduced arterial pressure compared to the S-nitroso albumin by alone.

7. The method according to claim 1, wherein administering the reduced glutathione together with the S-nitroso albumin results in reduced platelet aggregation compared to administering the S-nitroso albumin alone.

8. A method for the treatment of at least one of ischemia, cerebral ischemia, reperfusion injury, thrombosis, or hypertension, the method comprising: administering a pharmaceutical preparation to a subject in need thereof, wherein the pharmaceutical preparation comprises: a therapeutic protein having nitrosated SH-groups, wherein the therapeutic protein is S-nitroso albumin in one or more dosage of up to 10 µmol/kg/h; and reduced glutathione in one or more dosage of 12-140 µmol/kg/h so as to accelerates nitric oxide release by the S-nitroso albumin compared to administering the S-nitroso albumin alone.

9. The method according to claim 8, wherein administering the reduced glutathione together with the S-nitroso albumin results in enhanced treatment of ischemia compared to administering the S-nitroso albumin alone.

10. The method according to claim 9, wherein the method includes administering the S-nitroso albumin in one or more dosages of 0.035-1.0 µmol/kg/h and the reduced glutathione in one or more dosages of 12-140 µmol/kg/h.

11. A method for the treatment of at least one of ischemia, cerebral ischemia, reperfusion injury, thrombosis, or hypertension, the method comprising: administering a pharmaceutical preparation to a subject in need thereof the pharmaceutical preparation comprising: a therapeutic protein having nitrosated SH-groups wherein the therapeutic protein comprises S nitroso albumin in one or more dosage of up to 10 µmol/kg/h; and at least one thiol compound having a molecular weight of up to 10,000 daltons and comprising reduced glutathione in one or more dosage of 12-140 µmol/kg/h.

12. The method according to claim 11, wherein the pharmaceutical preparation comprises at least one additional thiol compound selected from the group consisting of L cysteine, L-cysteinyl glycine, y-glutamyl cysteine, and dihydrolipoic acid.

13. The method according to claim 11, wherein administering the at least one thiol compound together with the S-nitroso albumin results in enhanced treatment of ischemia compared to administering S-nitroso protein alone.

* * * * *

UNITED STATES PATENT AND TRADEMARK OFFICE
CERTIFICATE OF CORRECTION

PATENT NO. : 8,518,869 B2  
APPLICATION NO. : 10/599401  
DATED : August 27, 2013  
INVENTOR(S) : Hallström et al.

Page 1 of 1

It is certified that error appears in the above-identified patent and that said Letters Patent is hereby corrected as shown below:

In the Specifications

Column 3  
Line 14, change "FIG. 3B the effect" to --FIG. 3*b* shows the effect--

Column 6  
Line 3, change "$NO_2^-$—" to --$NO_2^-$--  
Line 60, change "applied IV simultaneously" to --applied via IV simultaneously--

Column 8  
Line 43, change "Determining the S-nitroso level" to --c) Determining the S-nitroso level--

Column 9  
Line 9, change "Providing reduced glutathione" to --d) Providing reduced glutathione--

In the Claims

Column 12  
Line 2, change "accelerates nitric oxide" to --accelerate nitric oxide--  
Line 16, change "in need thereof" to --in need thereof,--

Signed and Sealed this  
Tenth Day of December, 2013

Margaret A. Focarino  
*Commissioner for Patents of the United States Patent and Trademark Office*